United States Patent [19]
Kawakubo et al.

[11] Patent Number: 5,171,492
[45] Date of Patent: Dec. 15, 1992

[54] PROCESS FOR PRODUCING CARBONACEOUS IMPLANT MATERIAL

[75] Inventors: Takamasa Kawakubo, Gunma; Sugiro Ohtani, Kiryu, both of Japan

[73] Assignee: Mitsubishi Pencil Co., Ltd., Tokyo, Japan

[21] Appl. No.: 666,508

[22] Filed: Mar. 7, 1991

Related U.S. Application Data

[63] Contination of Ser. No. 343,281, Apr. 26, 1989, abandoned.

[51] Int. Cl.$^5$ .................. C01B 31/00; D04H 1/16
[52] U.S. Cl. ................... 264/296; 264/113; 427/249
[58] Field of Search ............ 264/29.6, 29.3, 109, 264/113; 623/16; 156/242; 427/249

[56] References Cited

U.S. PATENT DOCUMENTS

| | | | |
|---|---|---|---|
| 4,070,514 | 1/1978 | Eatherly et al. | 264/29.5 X |
| 4,351,069 | 9/1982 | Ballintyn et al. | 264/327 X |
| 4,456,645 | 6/1984 | Chi | 264/29.1 X |
| 4,542,539 | 9/1985 | Rowe, Jr. et al. | 623/16 |
| 4,698,189 | 10/1987 | Tetzlaff | 264/29.1 X |
| 4,846,834 | 7/1989 | von Recum et al. | 623/11 |

FOREIGN PATENT DOCUMENTS 2603456  8/1977  Fed. Rep. of Germany .... 623/16 E Primary Examiner—James Lowe
Assistant Examiner—Christopher A. Fiorilla
Attorney, Agent, or Firm—Oliff & Berridge

[57] ABSTRACT

An implant material for a living body hard tissue which is constructed by forming a core of a carbon material having a smooth and high hardness surface, an excellent mechanical strength against bending and compressing strengths, and non-impregnable to blood, lymph or the like and further forming a porous layer having a thickness of 100 microns or larger, preferably 100 microns or large on the surface of the core. This porous structure of the implant material is very important to smoothly and rigidly bond the material to a living body and is devised to produce the state that a collagen fiber newly produced in the boundary between the living body and the implant material is intruded into the porous tissue of the surface of the implant material and mutually interchanged, and a process for producing the same. Thus, the implant material has a smooth and high hardness surface, an excellent mechanical strength against bending and compressing strengths, and being non-impregnable to blood, lymph or the like.

6 Claims, 1 Drawing Sheet

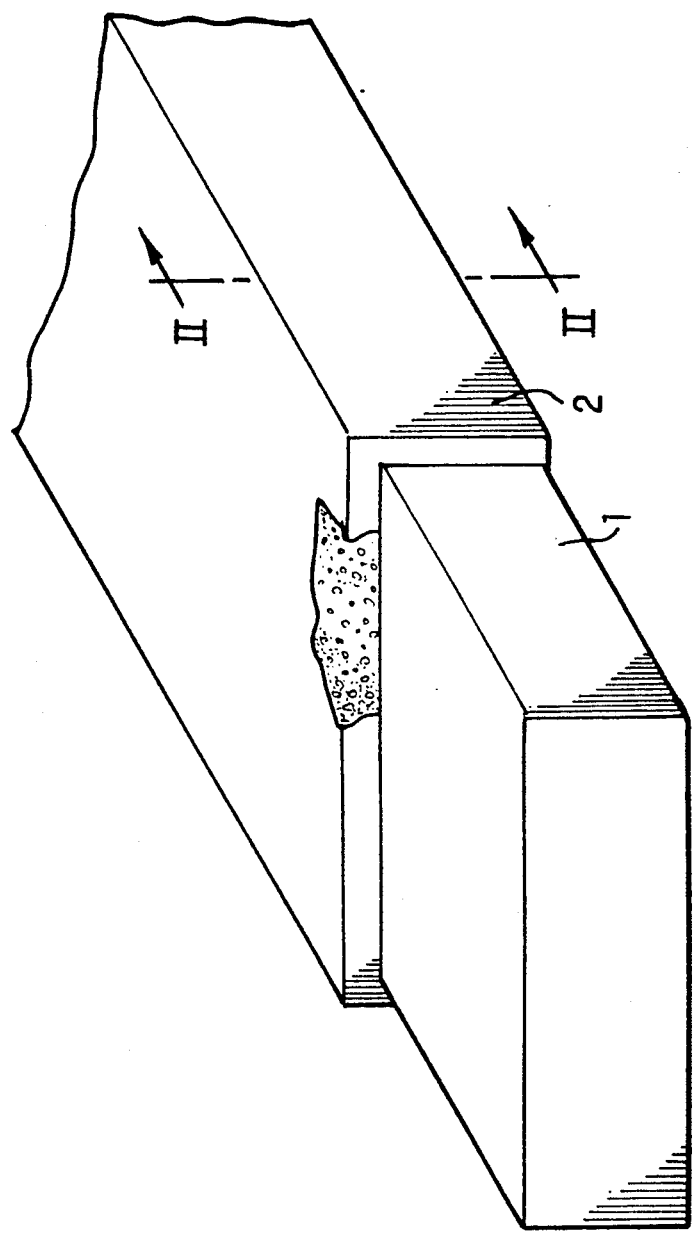
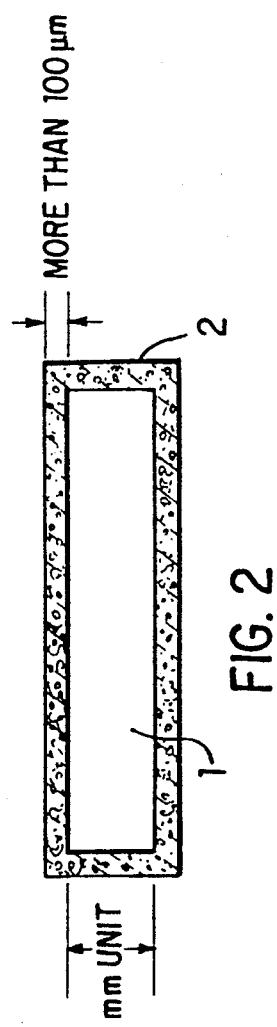

PROCESS FOR PRODUCING CARBONACEOUS IMPLANT MATERIAL

This is a continuation of application Ser. No. 07/343,281 filed Apr. 26, 1989, now abandoned.

BACKGROUND OF THE INVENTION

The present invention relates to an implant material (a material to be buried) for a living body hard tissue and a process for producing the same. More particularly, the invention relates to such an implant material for a living body hard tissue having less living body rejection, a proper affinity to the living body tissue, rigid coupling to tissue and excellent durability in vivo as materials of an artificial bone or tooth to fill or replace the defective portion of the bone or tooth and a process for producing the same.

Materials buried in vivo as artificial bone or tooth have heretofore been discussed and tried over a long period of years, but there are still a number of problems. Material such as ceramics, glass or carbon have been recently developed, instead of the conventional metal or high molecular resin material, and put to practical use.

The required properties of the implant material variously depend upon the shape, dimensions and function of the material at the implant position, and designs and selection of materials which have the required properties also depend largely upon the very difficult conditions present in the living materials.

The conditions of the implant material necessary to safely achieve the function in vivo are as follows:

(1) The implant material has no toxicity, no tissue stimulation, no carcinogenesis, no allergy, nor defects such as destructive action or the like of tissue in the vicinity.

(2) The material should not induce an immune reaction (which is an action of discharging the body out of the living body).

(3) The material should not be absorbed (decomposed or erased) in vivo.

(4) The material should not be ionized or dissolved by the influence of blood, lymph or the like.

(5) The material should have suitable affinity to the live body tissue and be bonded to it.

(6) The material should have high mechanical strength such as strength against compression, high durability against stress in use and resistance to deterioration in strength under a living body environment.

(7) The material should be readily handled and subjected to an easy sterilization.

(8) The material should be able to be adjusted in hardness and elasticity in a degree equal to or slightly larger than the hard tissue of the living body and to have a natural state as near as possible even if the material is integrated with the tissue.

When the materials are evaluated in comparison with the above-described requirements, the metal materials have problems in the conditions listed in the above paragraphs (1), (2), (4) and (8), and the plastic materials frequently have problems in the above paragraphs (2), (3) and (6). On the other hand, the ceramic materials which have been recently noted almost meet the conditions peculiar for the living body tissue in the above paragraphs (1) to (5). The reasons why the ceramic materials were not heretofore used were that they did not have sufficient mechanical strength listed in the above paragraph (6) and that the materials were disadvantageously deteriorated in strength under the environment in vivo with much water content. In this respect, the above drawbacks can be improved due to the developments of artificial sapphire single crystal, polycrystalline alumina material or sintered apatite hydroxide, which are partly employed in a practical use. However, the alumina material of the former has remarkably high hardness and elastic modulus, which causes problems such as an induction of defects in which a stress applied to the living body is concentrated at the buried material, unreasonable stress is acted in the environmental tissue to destroy the tissue and in an extreme case, is arrived at the tissue of a nerve, thereby damaging the nerve. Thus, the alumina material still remains insufficient under the requirement listed in the above paragraph (8). The sintered synthesized apatite hydroxide of the latter is a material which is extremely near the hard tissue of the living body and has less problems than in the case of the alumina material, but has insufficient mechanical strength, and is encountered in difficulties and complications in the synthesis, molding and sintering techniques of the apatite powder. Further, the following means are employed when repairing the position of broken bone in the normal living body hard tissue (bone and tooth) in operation, burying an artificial joint, and implanting an artificial tooth root so as to secure an implant material to the body:

(1) A method of self-locking the implant material to a bone tissue by devising in a structure or a shape.

(2) A method of mechanically securing by using screws and bolts, nuts.

(3) A method of bonding the implant material to the bone with an adhesive such as a medical cement. However, the implant material is slackened by any of the above methods for a long period of time, and even if the implant material itself does not have any defect, it is necessary in some cases to consider in case of exfoliating and replacing the implant material.

An implant material is buried and implanted as a dental root into an alveolar bone, and a dental crown is secured to the material in a dental treatment, in which case the above-described various hard implant material is used. This material has various shapes such as a natural dental root shape, a pin shape, a blade shape or a screw shape, and any of these materials is used by designing in response to the respective diseases.

In this case, the implant material is used over the tissue in vivo and the surface of the living body. Thus, it is particularly necessary to bond in the boundary between the material and the tissue. More specifically, it is important to bond at the portion which is projected from the living body into the surface of the implant material. If this technique cannot be preferably carried out, unpreferable results are induced due to the contamination of bacterias from the living body or the impregnation of detrimental substances.

In view of the present status that the above-described drawbacks and problems still remain at present, the inventor of the present invention has aimed at the points that carbon has been started to be noted as a material for a living body from the half life of 1960, has excellent antithrombotic properties, has no tissue stimulation, has a high affinity to the living body has, a remarkable stability under various environments in and out of the living body as well as excellent mechanical strength, with the result that a number of examples of success that an application of the carbon to an artificial heart valve has already been issued, and has also been employed in a practical use in ligaments, dental root materials and artificial joints. The inventor has further studied repeatedly the materials and structures in which the bond to the living body hard tissue becomes rigid, devised in designing the shape to provide sufficient strength in maintaining the functions of the living body, and has finally succeeded to create an excellent implant material for a living body hard tissue which could not heretofore be obtained.

SUMMARY OF THE INVENTION

Accordingly, an object of the present invention is to provide an implant material for a living body hard tissue and a process for producing the same which is smooth on the surface, protected and strengthened by employing as a core a dense carbonaceous material having high hardness, high strength and being non-impregnable characterized by constructing a tertiary porous carbonaceous layer having a thickness larger than 100 microns on the surface of the core to be formed substantially of only carbon, and is precipitated on the surface with gas phase thermal composition carbon as required by a covering treatment.

BRIEF DESCRIPTION OF THE DRAWINGS

A more complete understanding of the present invention can be obtained by reference to the accompanying drawings, wherein:

FIG. 1 is an enlarged schematic view of the core and carbonaceous tertiary material of the invention; and FIG. 2 is an enlarged sectional view of the line II—II of FIG. 1.

DETAILED DESCRIPTION OF PREFERRED EMBODIMENTS

According to the present invention, the implant material is constructed by forming a core, 1 (as shown in FIGS. 1 and 2) of a carbon material having a smooth and high hardness surface, an excellent mechanical strength against bending and compressing, and non-impregnation to blood, lymph or the like and further forming a porous layer 2 having a thickness of 100 microns or larger, preferably 500 microns or larger on the surface of the core. This porous structure of the implant material is very important to smoothly and rigidly bond the material to a living tissue and is devised to produce the state that a collagen fiber newly produced in the boundary between the living body and the implant material intrudes into the porous tissue of the surface of the implant material. Further, it is necessary to suitably distribute fine pores through which circulating liquid such as blood can be readily impregnated so as to supply oxygen and nutriments to the surface porous layer. More particularly, the implant material preferably has fine pores having a diameter of 50 microns or smaller, and preferably 20 microns or smaller in the vicinity of the core. With the fine pores of the above diameter, the collagen fiber tissue is impregnated internally into the implant material without impregnation of capillary blood vessels and is calcified to exhibit the state rigid bonding to the surface of the core, thereby developing an anchoring effect. In an intermediate layer adjacent to the porous layer having fine pores of diameter of 100 microns or less, it is preferable to distribute the fine pores of approx. 100 microns or larger, and more preferably approx. 200 microns. In this range, oxygen and nutriments can be sufficiently supplied via capillary blood vessels, and the collagen fiber tissue is secured in a softened state. In the further outermost surface, it is preferable to be constructed of a porous layer having a distribution of pores of a diameter of 600 microns or less and, more preferably 300 microns. In the outermost surface having the distribution of the pores of the above-described diameters, lymph and blood vessels can freely impregnate, thereby effectively enabling cell growth. Thus, the collagen fiber tissue can softly and rigidly bind the implant material to the living body hard tissue by means of the anchoring effect, thereby exhibiting state similar to that found in nature.

The porous layer in this case means in general the surface structure having a distribution of the pores having a designed diameter and high percentage of voids, which is constructed of fine particles of a high molecular weight organic material having a distribution of pores of managed diameter in general in which the particles are point bonded or point fusion-bonded to be rigidly sintered and calcined in isotropic property and to be carbonaceous porous material having voids in three dimensions. As described above, the implant material having significant functions according to the present invention may be employed in a practical use in the state remaining in three-dimensional point-sintered porous layer, but it is ideal to precipitate and deposit gas phase thermal decomposition carbon to cover the surface for the purpose of protecting and strengthening the surface structure and smoothing the surface to facilitate the bonding of cells. The covering treatment of the gas phase thermal decomposition carbon may employ, as thermal composition carbon, raw material hydrocarbon compounds such as benzene, naphthalene, and halogenated hydrocarbons such as dichloroethylene, trichloroethane, by maintaining the temperature of the material to be treated at a range of 600° C. to 2,300° C., and more preferably of 700° C. to 1,100° C. Particularly, when the halogenated hydrocarbon is employed, it has the advantage that the treatment can be carried out at lower temperatures. The time required to precipitate the gas phase thermal decomposition carbon and to deposit it depends upon the conditions, and is normally 1 to 10 hours. As described above, the function of increasing the cells and the affinity of the living body have been described as indispensable requirements of the implant material for the living body in terms of the structure of the carbonaceous tertiary porous material and the covering treatment of the gas phase thermal decomposition carbon.

A general process for producing carbonaceous tertiary porous material according to the present invention will now be described in more detail. Organic high molecular weight materials to be used as the raw materials of the porous material of solid particles may be any calcined in an inert gas phase atmosphere in general, and preferably comprise particles of a mixture of one or more of thermoplastic resins such as polychlorinated polyvinyl chloride resin, polyacrylonitrile resin, polyvinyl chloride resin, polyvinyl alcohol, polyphenylene ether resin, polyamideimide resin, polyimide resin, aromatic polyamide resin, polydivinyl benzene, and monomers of thermosetting resins such as furan resin, phenol resin, bismaleimidotriazine resin; or initial condensate polymer that is lightly cured to the thermally deformable degree or to the degree capable of being dissolved by a solvent and pulverized into particles; or natural high molecular weight particles having condensate polynuclear aromatic compounds such as tragacanth gum, Arabian gum; polysaccharide in the basic structure of the molecule; synthetic high molecular particles having condensate polynuclear aromatic compounds not contained in the above particles in the basic structure of the molecule, i.e., formalin condensate of naphthalenesulfonic acid, threne color and their intermediates, and petroleum asphalt, coal tar, whose synthetic resins are dry distilled at 300° C. to 500° C., and more preferably 380° C. to 400° C. to remove low molecular weight compounds, and be pulverized into particles. The shape of the organic high molecular weight particles used in this process is not particularly limited, but is preferably spherical shape. The size of the particles is preferably in diameter or in the maximum side of 1 mm or less and such that 90% or more of the particles preferably has a diameter or the maximum side of 30 microns or larger.

In order to increase the porosity (percentage of voids) of porous carbon, one may select the particles of larger diameter, and to decrease porosity on the other hand, one may select the particles of smaller diameter. In order to equalize the diameters of pores in the particles, the organic high molecular weight particles are classified in advance by a filter, air shifting or water shifting to equalize the diameters of the particles. In order to further form a multilayer three-dimensional structure having a distribution of porosity designed so that the central portion is dense and the outer surface portion is coarse, ultrafine particles, middle particles, and coarse particles, classified in advance to have uniform diameters, are respectively prepared. Then, flat plate molds for molding are heated, the ultrafine particles are first filled in the mold to lightly melt-bond (fusion-bond) the particles, the middle and coarse particles are then sequentially filled to melt-bond (fusion-bond) the particles thereby to integrate all the particles. For the purpose of imparting shape to the porous layer such as cylindrical, circular columnar, or square columnar shape, the particles are filled in the molds having these shapes to melt-bond (fusion-bond) the particles thereby to obtain a molding composition maintained in the shape of the molds. The heating temperature of the above-described molds is in a range of at least softening temperature to the melting point of the used organic high molecular particles to be adjusted to produce point fusion-bonds between the surface layers of the particles from the softening of the organic high molecular particles. In this case, if the temperature is excessively low, the resultant flowability of the particles from the softening decreases to cause no point fusion-bond to occur. If the temperature is, on the contrary, excessively high, the resultant flowability due to the softening increases. Accordingly, the pores of the porous material thus produced are unpreferably closed, or vanished in the extreme case. When the particles are point-bonded by a solvent, the solvent capable of dissolving the organic high molecular weight particles is added depending upon the dissolving capability, and is generally 10% by weight or less of the particles, and more preferably 5% by weight. The surfaces of the particles are uniformly moistened by a high speed agitator such as a Henschel mixer, and the moistened particles are then charged in the molds for molding similar to that described above. In this case, it is important to add the solvent in the quantity necessary to dissolve and point-bond only the surfaces of the organic high molecular weight particles. The porous material thus shaped is then dried to volatilize the solvent thereby to obtain the organic high molecular weight porous material. The organic high molecular weight porous material thus obtained according to any of the above-described processes is then post-cured, oxidized and crosslinked by heated air, or dipped in an acid such as thermal concentrated sulfuric acid thereby to subject it to a dehydrogenating reaction. Then, the resulting porous material is subjected to insolubilization and infusibilization to produce a preformed carbon.

Then, a process for producing a dense carbonaceous core material (which will be referred to as "a core") having a high hardness, high strength and being nonimpregnable according to the present invention will be described.

Any of the processes which will be described is employed as the process for producing the core.

A first process (1). Thermoplastic synthetic resins such as polychlorinated polyvinyl chloride resin, polyvinyl chloride resin, polyvinyl alcohol-vanillin-tragacanth gum mixed resin are used as a matrix, a carbonaceous powder such as natural graphite powder having high crystallinity, and carbon black or carbon fiber chopped fiber is added as a filler to the above resin thereby to produce a mixture. This mixture is then strongly kneaded by mixing rolls and a press kneader having high shearing force to induce a mechanochemical reaction in the boundary between the matrix resin and the carbonaceous powder, and subjected to a homogeneous dispersion until the carbonaceous powder preferably becomes primary particle state thereby to obtain a molding composition. Then, this composition is extruded under high pressure by an extrusion die of desired shape by an ordinary plunger type or screw type extruding machine thereby to obtain a molding for a core of the desired round rod (circular columnar), plate or square columnar shape.

A second process (2). A mixture of one or more of monomers, prepolymers of high molecular weight compounds, capable of being relatively readily condensed condensing thermally with a substance which exhibits high carbon residue yield after being calcined as a matrix, and low-duty condensate, is prepared. Carbonaceous powder similar to that in the first process (1) is then added to the mixture. The resultant mixture is then subjected to a homogeneous dispersion, is strongly kneaded by mixing rolls or a press kneader having high shearing force. Mechanical energy is produced by ball mills to induce a mechanochemical reaction, whereby the matrix resin is rigidly bonded physicochemically to the surface of the primary particles of the carbonaceous powder used as a filter thereby to obtain a molding powder composition. Subsequently, this composition is compression molded in a desired shape by an ordinary hot press molding machine to obtain a core molding.

Then, a process for constructing a carbonaceous tertiary porous material on the surface of the core, important in the process of the present invention, will be described.

The first process comprises the steps of burying (inserting) the core molding obtained by any of the above processes described in the above-described paragraphs (1) and (2) directly into the crude particles of the organic high molecular weight material as the raw material for the porous material, and producing a point-melt bond or point-fusion bond on the surface of the core and between the particles by heating or using a solvent, thereby obtaining a crude implant molding imparted in shape integral between the core and the tertiary porous layer. This crude implant molding is oxidized and crosslinked in an air bath heated at 50° C. to 300° C. and preferably at 150° to 200° C., or dipped in thermal concentrated sulfuric acid to subject it to a dehydrogenating reaction to insolubilize or infusibilize the implant molding, thereby producing preformed carbon. Then, the carbon is gradually heated in an inert gas phase such as nitrogen gas to calcine the carbon at a predetermined temperature such as 800° C. or higher to carbonize it, thereby obtaining a complete carbon product.

The second process comprises the steps of insolubilizing or infusibilizing in advance by any of the means for imparting the core obtained by the above process into a tertiary porous material by point-melt bonding or point bonding on the surface of the core molding to produce a porous material, then integrally bonding the porous materials with liquid or paste organic high molecular weight composition having a carbonizing bonding force as an adhesive property to obtain an implant molding. The liquid or paste organic high molecular weight composition used as the adhesive may comprise any compound having a strong bonding force in the carbonizing stage and in liquid or paste state such as furan resin or phenol resin and may not be particularly limited. At this time, the liquid resin composition is combined with carbon powder such as ultrafine graphite or carbon black of 5 to 50% by weight and more preferably 10 to 20% by weight to the liquid resin. This bonding is preferred since the composition can strengthen the carbonizing bond. A crude implant molding thus bonded integrally between the core and the porous layer is calcined and carbonized similarly to the first process thereby obtaining a complete product.

The third process comprises the steps of carbonizing the core and the porous material on the basis of the above-described calcining means, further integrally bonding the core and the porous material with the carbonized adhesive, and then recalcining the integrated material thereby obtaining a completely integrated carbonized product.

The implant material obtained by the above-described first, second and third processes is smoothed on the surface by precipitating, depositing and covering gas phase thermal decomposition carbon as required as described above and is simultaneously increased in the surface strength.

The implant material for the living body hard tissue of the present invention has the following properties:

(1) The impregnation of living body tissue and the hard bone tissue forming (ossifying) speed due to the calcining can be varied by suitably selecting and designing the structure and the diameter of the fine pores of the carbonaceous tertiary porous layer.

(2) The collagen fiber tissue end impregnated into the implant material is ossified on the surface of the core to be integrated, the intermediate layer is softly ossified, and the outer surface is covered with newly generated collagen fiber tissue to be integrated with the living body bone tissue, and the implant material is rigidly bonded by an anchoring effect, thereby exhibiting the state like the nature.

(3) The implant material has an antithrombotic property, extremely low tissue stimulation and excellent affinity, and is used without selecting the place to be applied.

(4) Since the entire implant material is composed of only carbon, the material is not corroded, and its mechanical properties are not deteriorated with age in the living body environment.

(5) Since the implant material has a light weight and elastic modulus similar to the living body tissue, unreasonable force due to the concentration of a stress is not applied to the living body.

(6) Since the implant material has a porous structure in the surface layer, the implant material has independent properties in case of operating, and can be freely applied to the position to be inserted. Accordingly, no slack occurs like the other hard material but the material can endure for a long period of time.

The present invention will now be described concretely with examples, and the present invention is not limited to the particular examples.

EXAMPLE 1

Round rod sample

As the material of a core molding composition, a polychlorinated polyvinyl chloride resin (T-025 produced by Nippon Carbide Industries Co., Ltd., Japan) having a mean polymerization of 800 and chlorine content of 64.6% was employed, 70% by weight of highly crystalline natural graphite ultrafine powder was added as a filler to 100% by weight of the polychlorinated polyvinyl chloride resin to produce a mixture. 25% by weight of dioctylphthalate was further added as a plasticizer to 100% by weight of the mixture. After the resultant mixture was dispersed in a Henschel mixer, the mixture was then sufficiently kneaded repeatedly by mixing rolls maintained at the surface temperature of 130° C., and continuously kneaded until the graphite particles approach the primary particle state to induce a mechanochemical reaction thereby to obtain a core molding composition.

This molding composition was then degassed by a vent type screw extruding machine, and simultaneously molded at the molding temperature of 150° C. thereby obtaining a round rod (crude molding) having a diameter of 2.5 mm. After this round rod was cut to a length of 20 mm, the rod was vertically placed in a cylindrical mold having a diameter of 5.0 mm. Then, the polychlorinated polyvinyl chloride resin (T-025) containing a mean polymerization of 800 and 64.6% chlorine was used for particles of the organic high molecular weight material. Material for a porous layer was classified by passing the particles through a filter of 30 mesh and collecting the remaining particles in a filter having 50 mesh. These particles were filled in the molds to the depth of 10 mm from the bottom, and then the entire molds were heat treated in an air oven of 160° C. for 30 min. The particles in the molds were then cooled at room temperature, were removed from the molds, and were point melt-bonded integrally to the surface of the core thereby obtaining an implant molding. Then, this molding was dipped in a thermally concentrated sulfuric acid heated to 100° C. for 20 min. to subject it to a dehydrochlorinating reaction and dehydrogenating reaction. The mold was then washed with water, and dried to subject it to insolubilization and infusibilization to produce a preformed carbon. Further, the carbon was heated to 500° C. at 10° C./hr. and then to 500° to 1,000° C. at 50° C./hr. in nitrogen gas, was then allowed to stand for 3 hours at 1,000° C. It was then cooled by allowing the carbon to stand to complete the calcination, thereby obtaining a complete implant material which was completely carbonized.

The diameters of fine pores formed in the porous layer on the surface of the implant material was 150 microns as a center in a range of ±50 microns in a distribution. The sample had a diameter of core of 2.1 mm, the maximum outer diameter of 3.6 mm and a length of 18.0 mm, a bending strength of 4,000 kgf/cm$^2$ and compression strength of 5,500 kgf/cm$^2$ as sufficient mechanical strengths.

EXAMPLE 2

Plate sample

As a core molding composition, the same material as that used in Example 1 was employed, and was extrusion molded by a plunger type hydraulic extrusion molding machine having a degassing unit at the molding temperature of 130° C. and the molding pressure of 70 kg/cm$^2$ into the molding having a thickness of 2.5 mm and a width of 30 mm. This molding was cut into a length of 25 mm thereby to obtain a plate (crude molding). Further, as a material for constructing a porous layer, a polychlorinated polyvinyl chloride (T-870 produced by Nippon Carbide Industries, Co., Ltd.) having a mean polymerization of 740 and chlorine content of 67.0% was employed. This material was classified in advance into (1) fine particles by filtration by first passing the material through a filter of 200 mesh (containing 90% of particles having a diameter of 45 microns or less), then into (2) middle particles by filtration by passing the material through a filter of 100 mesh and the remainder through a filter of 150 mesh (70 microns of mean diameter), and into (3) coarse particles by passing the material through a filter of 30 mesh and the remainder through a filter of 50 mesh (280 microns of mean diameter). Then, the fine particles described in the above number (1) were laid in a thickness of 1 mm on the molds having smooth surface of 200 mm (lateral)×300 mm (longitudinal) in size, and the molds were then heated to 150° C., allowed to stand in an air bath heated to 150° C. for 2 min., and were then cooled to room temperature thereby to obtain a porous layer in which the particles were lightly fusion-bonded. Then, the middle particle layer was placed on the fine particle layer, and the coarse particle layer was then placed on the middle particle layer. Similar operations were sequentially repeated thereby obtaining a crude molding of integrated tertiary porous material having a 3-layer structure of different distributions of fine pores. Subsequently, this material was insolubilized and infusibilized as in Example 1, then heated to 400° C. at the temperature rising speed of 10° C./hr. in nitrogen gas and then cooled thereby obtaining the tertiary porous material.

Liquid or paste adhesive having carbonized bondability was separately prepared. More particularly, 80% by weight of initial condensate of furan resin (Hita Furan VF-302 produced by Hitachi Chemical Co., Ltd., Japan) and 20% by weight of natural graphite powder (2 microns) were mixed, prepared and cooled to obtain liquid material by kneading the material with 3 rolls.

Then, the preformed carbon of the porous material was cut into 10 mm (longitudinal)×30 mm (lateral) in size. Two sheets of this material were bonded integrally by adding a mixture of the adhesive added suitably with a curing agent on the surface of the plate core between the front and the back surfaces to obtain a crude implant molding.

Subsequently, this material was calcined and carbonized under the same conditions as the Example 1, thereby obtaining the carbonaceous implant material to be an object.

In order to measure the diameters of fine pores forming the surface tertiary porous layer, the sample was cut. The observed diameters were 15 microns on average in the vicinity of the core, 200 microns on average in the intermediate, and 350 microns on average in the outer surface, and the layers were melt-bonded therebetween. The surface of the core and the surface of the porous layer were strongly bonded, and the boundary therebetween could not be identified.

The sample has a thickness of 4.8 mm (2.0 mm of core), a lateral size of 26 mm and a longitudinal size of 20 mm, a bending strength of 3,500 kgf/cm$^2$ and a compression strength of 5,800 kgf/cm$^2$ as sufficient mechanical strengths.

EXAMPLE 3

Blade sample

As a material of a core molding composition, 45% by weight of furnace black (MA-100 produced by Mitsubishi Chemicals Industries Limited, Japan) was added as a filler to 100% by weight of initial condensate of furan resin (Hita Furan VF-302 produced by Hitachi Chemical Co., Ltd., Japan) thereby to produce a mixture. After this mixture was uniformly mixed by a kneader, the mixture was sufficiently kneaded by mixing rolls maintained at a surface temperature of 50° C. was continuously kneaded until the graphite particles become a primary particle state to induce a mechano-chemical reaction and repeated until the furan resin was uniformly covered on the surfaces of the graphite particles. Then, the mixture was coarsely pulverized, charged in ball mills, and pulverized for 50 hours, thereby obtaining a core molding composition powder having a mean diameter of 5 microns. This composition powder was compression molded at a temperature of 150° C. and the molding pressure of 100 kgf/cm$^2$ by the molds thereby obtaining a core crude molding.

Then, the preformed carbon of the tertiary porous material having the 3-layer structure produced in Example 2 was cut and bonded integrally with the adhesive prepared in Example 2 to the front and back surfaces of the blade of the core to obtain an implant crude molding. Then, this implant molding was heat treated in an air oven heated to 180° C. for 10 hours to completely cure the molding thereby obtaining a preformed carbon.

Successively, this carbon was calcined and carbonized under the same conditions as in Example 1 thereby obtaining a carbonaceous implant material. The structure of the surface porous layer thus obtained was similar to Example 2. Further, this sample was hard on the surface, exhibited vitreous state, and had a bending strength of 1,500 kgf/cm$^2$, an elastic modulus of $2 \times 10^5$ kgf/cm$^2$, and a compression breakdown actual load of 240 kg, thereby exhibiting preferable properties as an implant material for a living body hard tissue.

EXAMPLE 4

Surface covering by gas phase thermal decomposition carbon precipitation

A plate material as the core was heated by direct energization of an electricity by securing the carbonaceous implant sample produced in the Example 2 as a base material. The depositing conditions were as follows:

| | |
|---|---|
| Raw organic material: | cis-1,2-dichloroethylene |
| Carrier gas: | argon |
| Raw gas concentration | 14 vol. % |
| Raw gas flow rate | 400 ml/min. |
| Surface temp. of central core: | 900° C. |

Further, the time required for completion of the deposition was 5 hours.

The surface of the implant material covered with the gas phase thermal decomposition carbon was very rigid and hard, and could not be scratched by a steel file.

The porous structure forming the surface layer of the implant material was excellently maintained, and according to the observation by an electron microscope, the surface of the sintered particle material was covered homogeneously, and smooth in round shape. The strength of the plate sample was further increased to provide a bending strength of 4,200 kgf/cm$^2$ and a compression strength of 6,500 kgf/cm$^2$.

The present invention has been described in terms of the Examples. However, these samples were observed in suitability as an implant material buried in an animal's alveolar bone and lower waist bone of monkey having a body weight of 4 kg.

What is claimed is:

1. A process for producing an implant material for a living body hard tissue, comprising:

mixing an organic high molecular weight resin and a carbonaceous powder to produce a homogeneous dispersion;

forming a dense core from said homogeneous dispersion;

forming a layer of porous carbonaceous material on the core, the porous layer being formed from organic high molecular weight particles which are point fusion-bonded to each other by application of heat or solvent;

producing preformed carbon in the porous layer by at least one of curing, insolubilizing and infusibilizing the bonded material;

calcining the bonded material to produce an integrated carbon implant; and depositing a surface layer on said implant via precipitation of a thermal gas phase carbon composition.

2. The process of claim 1, wherein said core comprises a thermoplastic resin and said carbonaceous powder is selected from the group consisting of graphite, carbon black, and carbon fiber.

3. The process of claim 1, wherein said core comprises a mixture of one or more organic monomers and said carbonaceous powder is selected from the group consisting of graphite, carbon black, and carbon fiber.

4. The process of claim 1, wherein said calcining comprises heating to at least 800° C.

5. The process of claim 1, wherein said layer of porous carbonaceous material is formed by point-melt bonding high molecular weight organic particles of about 30 mesh.

6. The process of claim 1, wherein said porous layer is produced by forming three outer layers upon said dense core, wherein said outer layers comprise a first outer layer of: fine organic high molecular weight particles of about 200 mesh; a second outer layer of medium organic high molecular weight particles of about 100 mesh; and a third outer layer of coarse organic high molecular weight particles of about 30 mesh; and wherein the order of the outer layers from the core is first, second and third.

* * * * *